(12) United States Patent
Larbouret et al.

(10) Patent No.: US 8,158,764 B2
(45) Date of Patent: Apr. 17, 2012

(54) MORPHINE DERIVATIVES

(75) Inventors: Karine Larbouret, Vergeze (FR); Roger Lahana, Nimes (FR); Cedric Castex, Reims (FR)

(73) Assignee: Neorphys, Nimes (FR)

( * ) Notice: Subject to any disclaimer, the term of this patent is extended or adjusted under 35 U.S.C. 154(b) by 155 days.

(21) Appl. No.: 12/444,430

(22) PCT Filed: Oct. 11, 2007

(86) PCT No.: PCT/FR2007/052122
§ 371 (c)(1),
(2), (4) Date: Apr. 6, 2009

(87) PCT Pub. No.: WO2008/043962
PCT Pub. Date: Apr. 17, 2008

(65) Prior Publication Data
US 2010/0075912 A1    Mar. 25, 2010

(30) Foreign Application Priority Data
Oct. 12, 2006   (FR) .................................. 06 54247

(51) Int. Cl.
C07H 17/02       (2006.01)
A01N 43/04       (2006.01)
A61K 31/70       (2006.01)

(52) U.S. Cl. .................... 536/17.4; 536/17.9; 536/17.5; 514/25; 514/27

(58) Field of Classification Search .................. 536/4, 7, 536/17, 18; 514/25, 27
See application file for complete search history.

(56) References Cited

U.S. PATENT DOCUMENTS 7,365,055 B2 *  4/2008  Temsamani et al. ............ 514/27
7,576,207 B2 *  8/2009  Dolle et al. ..................... 546/17

FOREIGN PATENT DOCUMENTS

| EP | 0 816 375 A1 | 1/1998 |
| EP | 0 597 915 B1 | 11/1998 |
| EP | 1 086 114 B1 | 10/2002 |
| EP | 0 960 111 B1 | 11/2004 |
| WO | 95/05831 A1 | 3/1995 |
| WO | 98/46618 A1 | 10/1998 |
| WO | WO98/54196 A1 * | 12/1998 |
| WO | 2005/063263 A1 | 7/2005 |
| WO | 2006/073396 A1 | 7/2006 |

OTHER PUBLICATIONS

Preechagoon, D.; Brereton, I.; Staatz, C.; Prankerd, P.J., International Journal of Pharmaceuticals, 1998, 163, 177-190.*
Black, S. L.;Jales, A. R.; Brandt, W.; Lewis, J. W.; Husbands, S. M., J. Med. Chem, 2003, 46, 314-317.*
Thornber, C. W., Chem. Soc. Rev., 1979, 8, 563-580.*
Aasvang, E. K.; Møhl, B.; Bay-Nielsen, M.;Kehlet, H., Pain, 2006, 122, 258-263.*
Gonen et al., Prevalence of Premature Ejaculation in Turkish Men With Chronic Pelvic Pain Syndrome, Journal of Andrology, 2005, 26, 601-603.*
Janssen et al., A New Series of Potent Analgesics Dextro 2: 2-Diphenyl-3-Methyl-4-Morpholinobutyrlpyrrolidine and Related Amides Part I. Chemical Structure and Pharmacological Activity, Journal of Pharmacy and Pharmacology, 1957, 9(1), 381-400.*
Patani, G. et al. "Bioisosterism: A Rational Approach in Drug Design" *Chemical Reviews*, 1996, pp. 3147-3176, vol. 96, No. 8.
Wlodek, L. "Beneficial and Harmful Effects of Thiols" *Polish Journal of Pharmacology*, 2002, pp. 215-223, vol. 54.
Thermo Scientific Pierce Crosslinking Technical Handbook, 2009, pp. 1-48.
Held, K. D. et al. "Mechanisms for the Oxygen Radical-Mediated Toxicity of Various Thiol-Containing Compounds in Cultured Mammalian Cells" *Radiation Research*, Jul. 1994, pp. 15-23, vol. 139, No. 1.
Mariona Salvatella, et al; "A highly toxic morphine-3-glucuronide derivative", Bioorganic & Medicinal Chemistry Letters 2004, 14(4), 905-908 Coden: BMCLE8; ISSN: 0960-894X, 2004, XP002434809.
Abdulghani A. Houdi,et al; "3-O-Acetylmorphine-6-0-Sulfate: A Potent, Centrally Acting Morphine Derivative", Pharmacology, Biochemistry and Behavior (1996), 53(3), 665-71 Coden: PBBHAU; ISSN: 0091-3057, 1996, XP002434810.
International Search Report: PCT/FR2007/052122, Mar. 2008, 3 pages.

* cited by examiner

*Primary Examiner* — Eric S Olson
*Assistant Examiner* — Zhengfu Wang
(74) *Attorney, Agent, or Firm* — Saliwanchik, Lloyd & Eisenschenk

(57) ABSTRACT

The present invention relates to new morphine-6-glucuronide derivatives, to pharmaceutical compositions thereof and uses thereof.

11 Claims, 7 Drawing Sheets

Figure 1
Synthesis of C6G-Cya
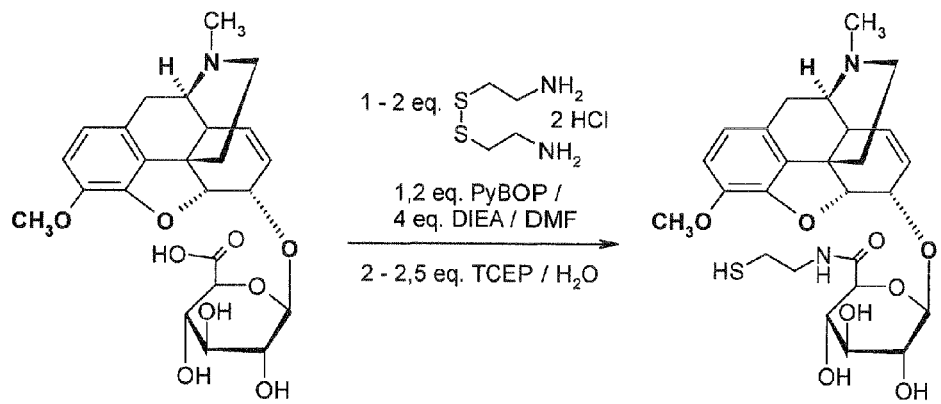
Synthesis of M3Et-6G-Cya
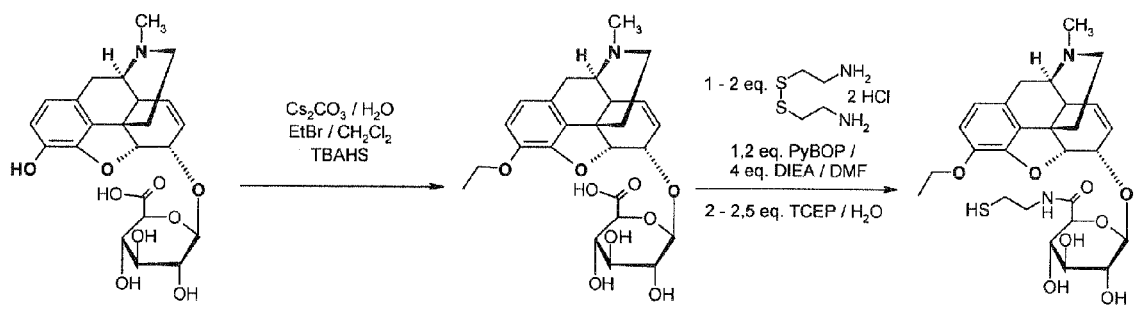
Synthesis of M3Et-6G-Cya-cya-M3Et-6G
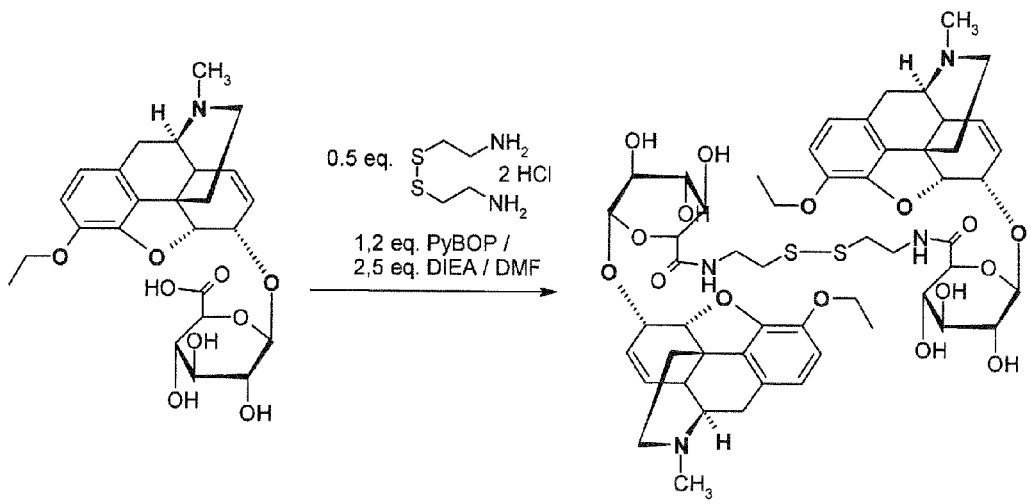

Synthesis of M3iPro-6G-cya-cya-M3iPro-6G

Synthesis of M3Et-6G-eva-3MP-NTI

Figure 2: Analgesic activity of compounds in the Tail flick test
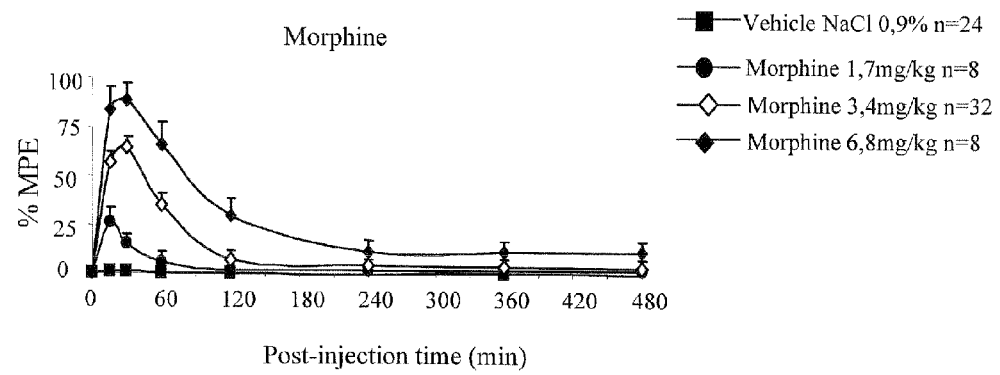
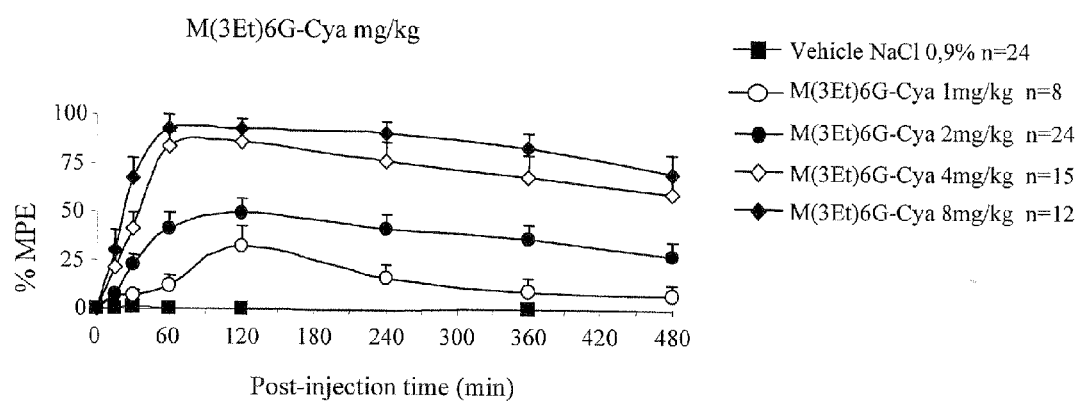
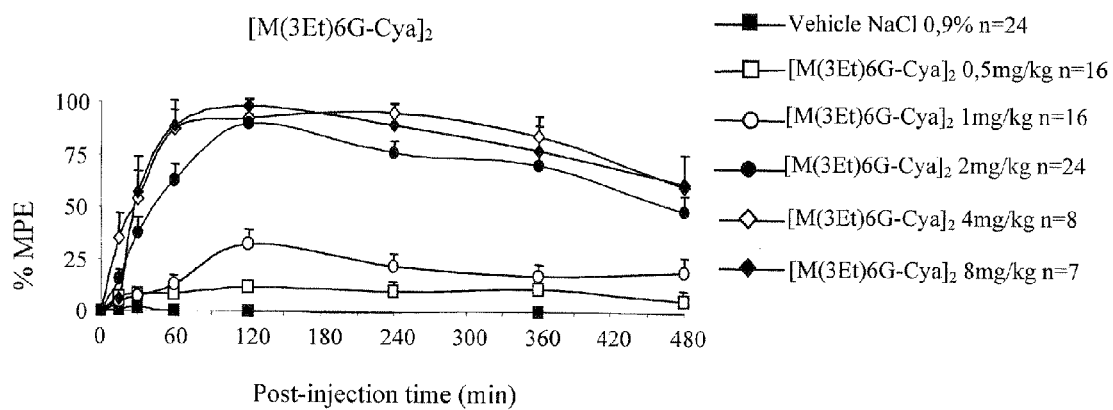

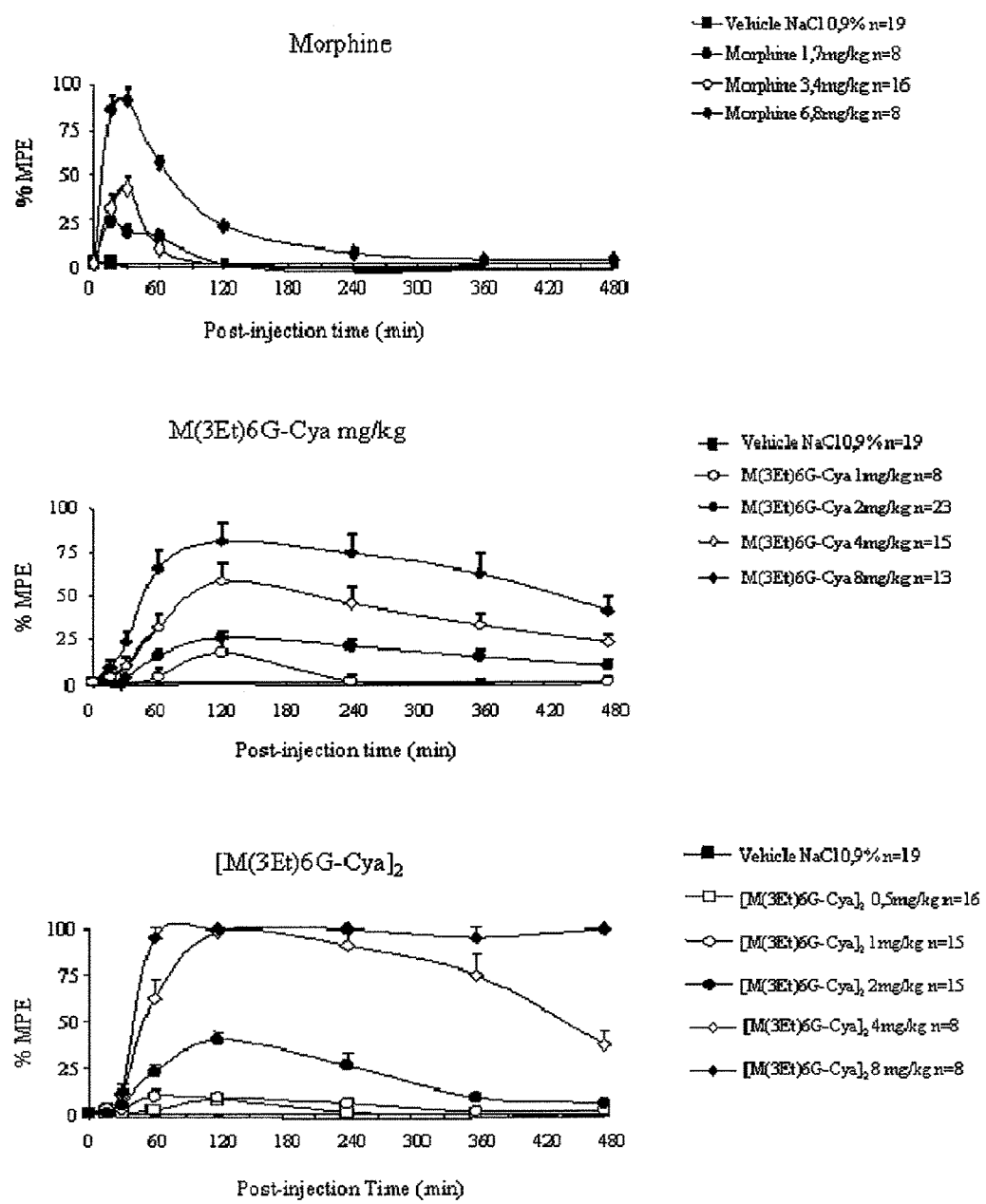
Figure 3 : Analgesic activity of compounds in the Hot plate test

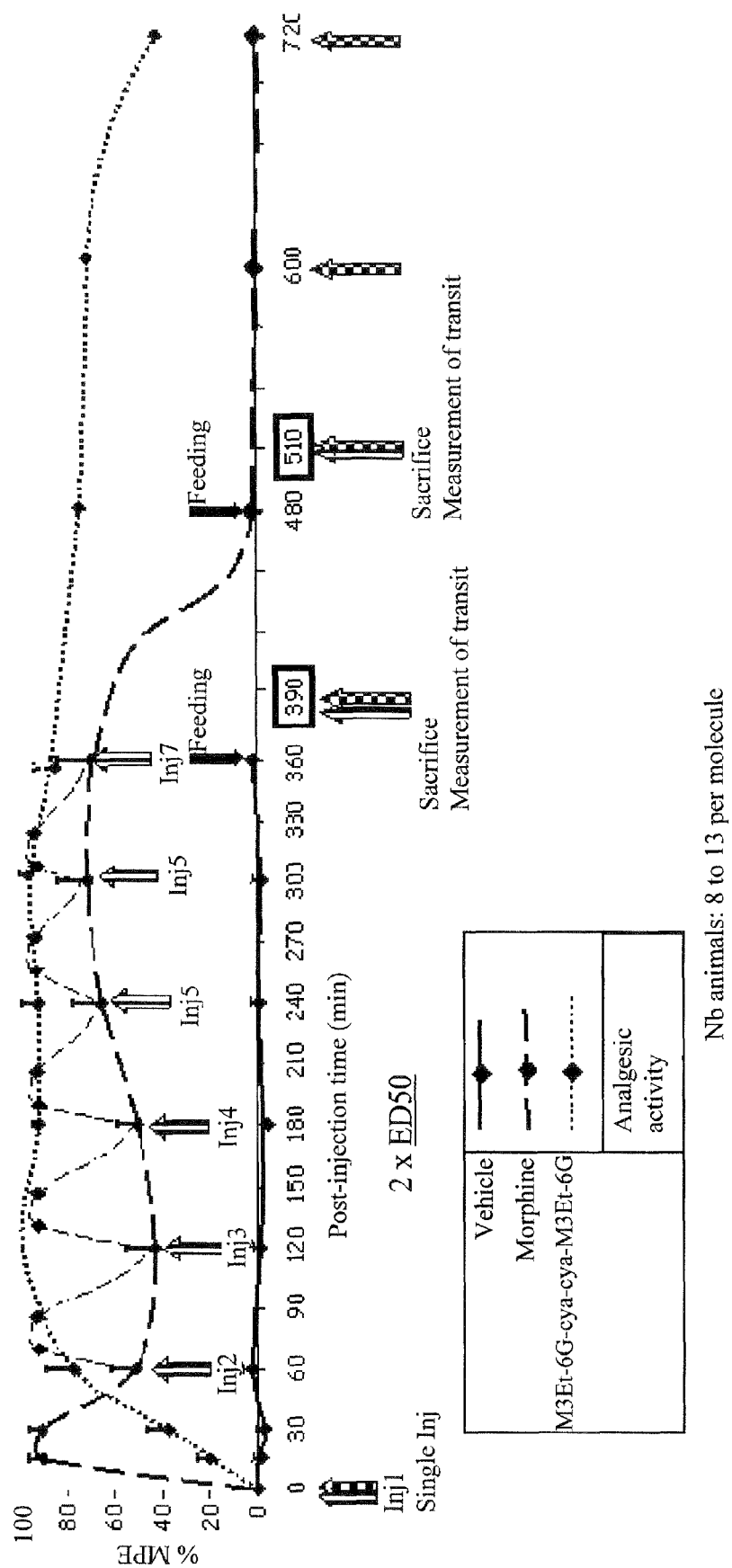

Results:

MORPHINE DERIVATIVES

FIELD OF APPLICATION

The present invention relates to new morphine derivatives, pharmaceutical compounds containing said new morphine derivatives and their use for pain management and sexual dysfunction.

DESCRIPTION OF THE CONTEXT OF THE INVENTION

Morphine is currently the drug of choice to treat acute pain whatever the intensity of the pain. This opioid drug is used in about 80% of cases of postoperative acute pain. Despite a high efficiency, use of morphine implies numerous side effects, specific to opioids, such as respiratory depression, nausea, vomiting, inhibition of intestinal transit, addiction and tolerance (Minoru Nariata et al., 2001, Pharmacol & Ther, 89, 1-15).

There are three main classes of opioid receptors: Mu ($\mu$), Kappa ($\kappa$) and Delta ($\delta$), all belonging to the family of G protein coupled receptors. Western Blot analysis, FRET (Fluorescence Resonance Energy Transfer) and BRET (Bioluminescence Resonance Energy Transfer) have highlighted monomers and dimers of these three types of receptors. (George S R et al., J Biol Chem 2000, 275: 26128-26135; Jordan B A et al., Nature 1999, 399:697-700; Gomes I et al., J. Neurosci 2000, 20: RC110.). Dimers may be either homodimers or heterodimers. This oligomerisation interferes with the physiologic role of opioid receptors and constitutes a new therapeutic approach of high potential.

As a matter of fact, opioid derivatives, once synthesized under dimer shape, show a better affinity and are more efficient than monomers for $\mu$, $\delta$ and $\kappa$ receptors (Hazum et al., Biochem Biophys Res Comm 1982, 104:347-353). Their analgesic activity, after intravenous administration, is higher and their duration of action, longer (WO2005/063263). This latest characteristic enables to decrease the number of administrations while maintaining a maximal analgesic activity, when compared with monomers and other opioids, such as morphine, which exhibits a shorter duration of activity.

Moreover, numerous studies (Gomes I et al., J Neurosci 2000, 20: RC110.) have shown a colocalization of $\mu$ and $\delta$ receptors on one hand and of $\delta$ and $\kappa$ receptors on the other hand, making physiologically possible the existence of heterodimeric receptors. Such hypothesis has been confirmed by FRET analysis, immunoprecipitation and binding profiles (Rios et al., Pharm & Ther 2001, 92: 71-87).

From a pharmacologic point of view, the interaction of a molecule with opioid receptors results in a more or less important analgesic activity as well as side effects.

For instance, binding to $\mu$ receptors is largely responsible for the analgesic activity of the molecule. Two sub-types of $\mu$ receptors exist: the $\mu$1 sub-type, with a strong affinity and a poor capacity, and the $\mu$2 sub-type, with a poor affinity and a strong capacity (Pasternak & Wood, 1986, Life Sci 38: 1889-1898). The interaction with $\mu$1 receptors results in an analgesic supraspinal reaction combined with a decrease of the turnover of the acetylcholine, whereas the interaction of $\mu$2 receptors results in an analgesic spinal action, commonly known for generating respiratory depression and inhibition of the intestinal transit.

$\kappa$ and $\delta$ receptors play a role especially in intestinal motility and analgesic activity. Moreover, their inhibition contributes to decrease the phenomenon of dependence and respiratory depression. (Rothman et al., 2000, J Subst Abuse Treat 19: 277-281, Shook et al., 1990, Am Rev Respir Dis 142: 895-909, J Neurosci 2005 Mar. 23; 25(12):3229-33. J Pharmacol Exp Ther. 2001 May; 297(2):597-605, J Pharmacol Exp Ther. 1998 December; 287(3):815-23).

These receptors are present in the central nervous system, especially at the level of the dorsal horn of the spinal cord and also at a peripheral level (Stein et al., 1995, Ann Med, 27(2): 219-21, Janso, Stein, Curr Opin Pharmacol, 2001, 1(1): 62-65).

Most identified side effects, such as respiratory depression, nausea, dependence and addiction, are central effects. A way to limit undesirable effects while maintaining an analgesic activity is to design opioids that both interact with the peripheral system and slowly diffuse into the brain (C. Stein, 1990, J of Pain and Symptom Management 6(3): 119-124; Zajaczowska R, Reg Anesth Pain Med, 2004, 29(5): 424-429; Likar et al., 1998, Pain 76(1-2): 145-50; Tokuyama et al., Life Sci, 1998, 62(17-18): 1677-81; Junien, Aliment Pharmacol Ther, 1995, 9(2): 117-26, Dehave-Hudkins et al., J Pharmacol Exp Ther, 1999, 289(1): 494-502, Stein et al., N Engl J Med, 1991, 325: 1123-1126). Indeed, activating opioid receptors of the central nervous system seems to remain the most efficient way to obtain an analgesia comparable with the one obtained with morphine.

Some bivalent ligands were designed and synthesized in order to interact with $\mu$/$\delta$ heterodimers. In that respect, Daniels et al. studied ligands that were constituted of a $\mu$ receptor agonist, oxymorphone, linked with a $\delta$ receptor antagonist, naltrindole (Daniels et al., PNAS 2005, 102(52): 19208, WO 2006/073396). The latter is well-known in literature as a specific $\delta$ receptor antagonist. They have obtained an analgesic activity for the dimer comparable with oxymorphone by intracerebroventricular administration and a significant decrease of phenomenons of tolerance and physical dependence. Moreover, it appears that these dimers act at the central level. Indeed, their ED50 and the one of morphine appear to be comparable after intravenous and intracerebroventricular (i.c.v) administrations.

It is commonly known that morphine undergoes an important metabolism that leads to the formation of Morphine-6-Glucuronide (M6G). This metabolite poorly enters into the brain, because of its hydrophilic nature. Its analgesic activity appears stronger than the one induced by morphine, when centrally administered, whereas nausea and vomiting decrease (Paul et al., 1989. J. Pharmacol. Exp. Ther. 251; 477-483; Frances et al., 1992. J. Pharmacol. Exp. Ther. 262; 25-31). However, it may provoke, like morphine does, a syndrome of addiction. Moreover, like all metabolites, it is rapidly eliminated by the organism. M6G shows a higher $\mu$ affinity (or a comparable one, depending on the studies) than the one shown by morphine, whereas $\kappa$ affinity is lower (Current Topics in Medicinal Chemistry, 2005, 5, 585-594).

M6G seems therefore to be an interesting basis to design an opioid as efficient as morphine without its undesirable side effects.

M6G has been produced by synthetic ways since 1968 (Hidetoshi et al., 1968) and its analgesic properties were highlighted in numerous publications (for instance, Frances et al., 1982, Kilpatrick et al.). EP 597 915 B1 and U.S. Pat. No. 6,046,313 patents describe the synthesis of M6G and M6G derivatives especially at position 3 and EP 1086114 B1 relates to a selective process of synthesis of $\beta$ anomer of M6G. WO 95/05831 application relates to the use of M6G by oral administration to treat pain.

M6G derivatives have been described. For instance, the EP 975 648 B1 patent claims specifically protection for an M6G derivative, wherein the bond between atoms of carbon 7-8 is saturated. The WO2005/063263 application describes sulfured M6G derivatives by substitution thanks to a group carrying a thiol function or a sulfur atom. These sulfur derivatives show a high analgesic activity and less side effects.

Opioid derivatives conjugated to carbohydrates, alternative to M6G and its derivatives, have been described in the EP 816 375 patent application.

However, the need to develop morphine derivatives showing higher analgesic activity and lower side effects remains.

DESCRIPTION OF THE INVENTION

The main object of the present invention is novel M6G derivatives, preferably dimeric or bivalent ligands, showing a strong analgesic activity, a longer duration of action and less side effects than currently used opioids. These derivatives have been designed:
- to slowly diffuse at the central level, by modulating the hydrophobicity of the made chemical modifications,
- to interact with receptors to either homodimer or heterodimer opioids,
- to show a strong affinity to μ receptors while inhibiting κ and/or δ receptors in order to decrease some side effects.

Inventors have established that the addition of a group carrying a thiol function on the carboxylic acid of the M6G glucuronide group and the modification of hydroxyl in position 3 especially by an ether function would enable to obtain compounds showing both a strong μ and κ affinity along with a strong analgesic activity. These properties are particularly accurate with dimerized compounds or bivalent ligands, obtained by oxydation of thiol functions and then formation of a disulfide bridge.

Literature showed that disulfide bonds could improve in vivo properties of active molecules: these bonds, relatively stable in plasma, are cleaved in cells (G. Saito et al., Advanced Drug Delivery Reviews, 2003, 55, 199-215).

The intended effect of these substitutions is a modification of the pharmacologic profile in comparison with already known M6G derivatives.

The group in position 3 is chosen with a view to increase the lipophylicity of M6G and to improve its central analgesic activity by favouring its crossing of the blood brain barrier (BBB). Literature however showed that some modifications of the hydroxyl in position 3 of the morphinic moiety provoked a loss of analgesic activity, and even toxicity (Abdulghani A Houdi et al., 1996, Pharm Biochem and Beh, 53 (3), 665-671; Salvatella et al., 2004, Biiorg & Med Chem. Lett., 14, 905-908). Inventors showed that a substitution in position 3 by a methoxy group (derivative of 6-codein-glucuronide) leads to an inactive and toxic compound (see example 1). The obtained result for the compounds according to the present invention is therefore unexpected.

A second application of these M6G derivatives regards sexual dysfunction and especially male premature ejaculation. Indeed, the efficiency of analgesic administration to treat premature ejaculation has been shown in literature (Eledjam & Safarinejad et al., Cah Anesthesiol. 1991; 39(2): 111-4), for instance local application of analgesics such as lidocaine, tramadol injection (Safarinejad et al., J Clin Psychopharmacol. 2006; 26(1): 27-31, US 2003/0186872 A) or even use of pharmaceutical preparations containing a mix of Viagra/delta opioid receptor agonist (U.S. Pat. No. 6,974,839).

The present invention relates therefore to a compound of Formula (A):

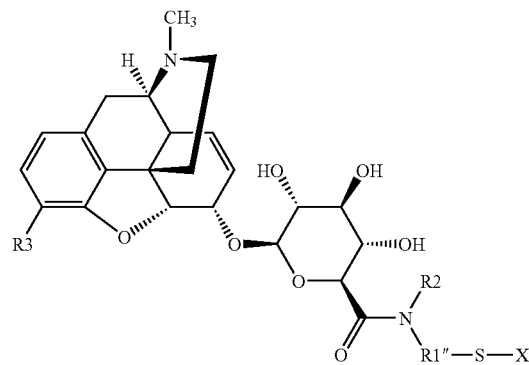

wherein the whole entity (A), except for the X substituent, is called $M_{R3}6G\text{-}NR_1R_2\text{---}S$;

R1 represents a $C_1\text{-}C_{10}$ alkyl group, the alkyl chain being possibly interrupted by one or several heteroatom(s) chosen among O, S and N;

R2 represents a hydrogen, a $C_1\text{-}C_5$ alkyl group, saturated or unsaturated, linear or branched, or an aryl, heteroaryl or ($C_1$-$C_5$) alkylaryl group;

R3 represents a Y(C=Z)R or YR group, Y and Z representing independently oxygen or sulfur, R being a $C_1\text{-}C_6$ alkyl group, linear or branched, saturated or unsaturated, provided that R3 is different than O—CH$_3$;

X represents a hydrogen, a radical —S—R4-W, or a radical $M_{R3}6G\text{-}NR_1R_2\text{---}S$, with R4 being a $C_1\text{-}C_8$ alkyl group that may contain amide, ester, ether bonds and W being either a δ receptor antagonist, or a κ receptor antagonist, as well as one of its pharmaceutically acceptable salts.

When R1 is a substituted alkyl, the substituent may be chosen among the group consisting of a $C_1\text{-}C_5$ alkyl group, saturated or unsaturated, an amino group, a COOR5 group; a CONR5R6 group, R5 and R6 representing independently hydrogen, a saturated or unsaturated $C_1\text{-}C_{20}$ alkyl group, optionally substituted, an aryl, an heteroaryl; a $C_1\text{-}C_{20}$ alkyl, preferably in $C_1\text{-}C_{10}$; bearing an aldehyde function and/or a ketone When R2 is substituted, the substituent may be a saturated or unsaturated $C_1\text{-}C_4$ alkyl group.

Preferably, when W is a δ receptor antagonist, it is chosen among the group consisting of naltrindole, naltriben, 7-benzylidenenaltrexone (BNTX), and 7-(5',6'-benzo-2'-spiro-indanyl)naltrexone (BSINTX).

When W is a κ receptor antagonist, it is chosen among the group consisting of 5'-guanidinonaltrindole and nor-binaltorphimine (nor-BNI). The radical W is linked to R4 so as to retain its antagonist activity.

When X represents a radical $M_{R3}6G\text{-}NR_1R_2\text{---}S$, radicals R1, R2 and R3 on both radicals $M_{R3}6G\text{-}NR_1R_2\text{---}S$ may either be similar or different.

An alkyl designates a saturated or unsaturated hydrocarbonated radical, linear or branched, substituted or not substituted. A $C_1\text{-}C_{10}$ alkyl group refers to a radical such as the one above defined presenting 1 to 10 atoms of carbon, preferably a group chosen among a methyl, ethyl, propyl, isopropyl, butyl, isobutyl, tert-butyl, pentyl, hexyl, heptyl, octyl, nonyl and decyl. A $C_1\text{-}C_5$ alkyl group refers to a radical such as the one above defined presenting 1 to 5 atoms of carbon, for instance a group chosen among a methyl, ethyl, propyl, isopropyl, butyl, isobutyl, tert-butyl and pentyl. A $C_1$-$C_4$ alkyl group refers to a radical such as the one above defined presenting 1 to 4 atoms of carbon, especially a group chosen among a methyl, ethyl, propyl, isopropyl, butyl, isobutyl, and tert-butyl. A $C_1$-$C_6$ alkyl group refers to a radical such as the one above defined presenting 1 to 6 atoms of carbon, especially a group chosen among a methyl, ethyl, propyl, isopropyl, butyl, isobutyl, tert-butyl, pentyl and hexyle. A $C_2$-$C_6$ alkyl group refers to a radical such as the one above defined presenting 2 to 6 atoms of carbon, especially a group chosen among an ethyl, propyl, isopropyl, butyl, isobutyl, tert-butyl, pentyl and hexyle. A $C_1$-$C_8$ alkyl group refers to a radical such nitrogen, sulfur and oxygen, substituted or not, having preferably 6 to 14 atoms of carbon. For example, one may mention groups such as pyridinyl, pyridazinyl, pyrimidyl, pyrazyl, triazinyl, pyrrolyl, pyrazolyl, imidazolyl, (1,2,3) and (1,2,4)triazolyl, pyrazinyl, pyrimidinyl, tetrazolyl, furyl, thienyl, isoxazolyl, thiazolyl, isoxazolyl or oxazolyl, etc.

The word <<alkylaryl>> designates an aryl-type radical substituted by an alkyl group. Words <<alkyl>> and <<aryl>> correspond with previously detailed definitions. Examples of alkylaryl groups are tolyl, mesythyl and xylyle.

More precisely, the present invention relates to morphine derivatives represented by formulae (B), (C) and (D):

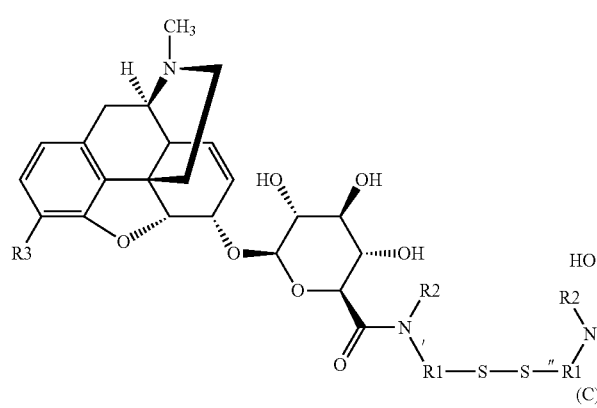

(B)

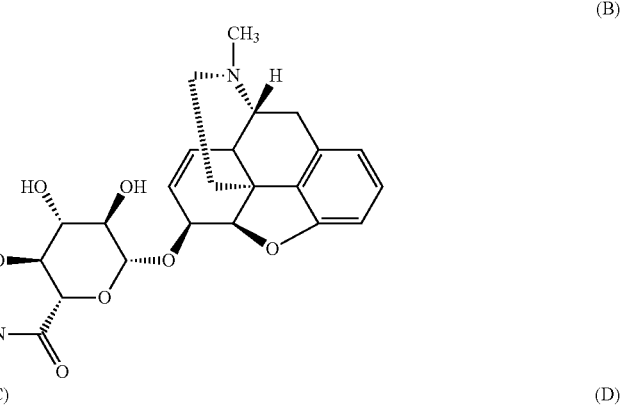

(D)

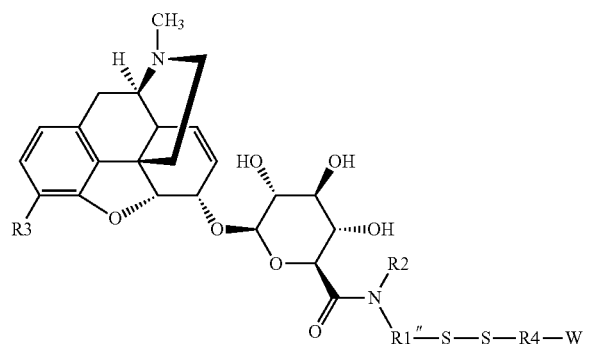

(C)

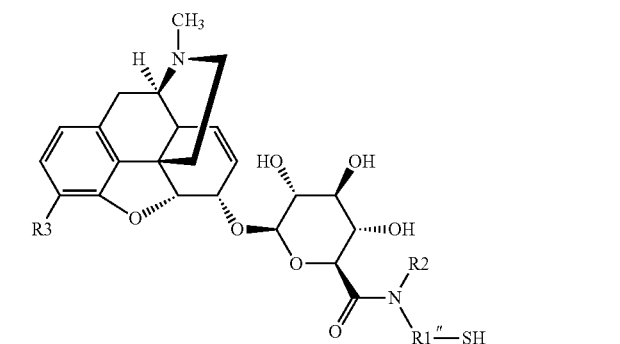

as the one above defined presenting 1 to 8 atoms of carbon, preferably a group chosen among a methyl, ethyl, propyl, isopropyl, butyl, isobutyl, tert-butyl, pentyl and hexyle, heptyl and octyl. A $C_1$-$C_3$ alkyl group refers to a group such as the one above defined presenting 1 to 3 atoms of carbon, preferably a group chosen among a methyl, ethyl, propyl and isopropyl. A $C_2$-$C_3$ alkyl group refers to a group such as the one above defined presenting 2 to 3 atoms of carbon, preferably a group chosen among an ethyl, propyl and isopropyl. A $C_1$-$C_4$ alkyl group refers to a group such as the one above defined presenting 1 to 4 atoms of carbon, preferably a group chosen among a methyl, ethyl, propyl, isopropyl, butyl, isobutyl and tert-butyl.

The word "aryl" designates an aromatic hydrocarboned radical, substituted or not, having preferably 6 to 14 atoms of carbon. Preferably, aryl radicals according to the invention are chosen among phenyl, naphtyl (for instance (1-naphtyl or 2-naphtyl), biphenyl (for instance, 2, 3 or 4 biphenyl), anthryl or fluorenyl. Phenyl groups, substituted or not, are particularly favoured.

The word "heteroaryl" designates an aromatic hydrocarboned radical comprising one or several heteroatoms such as wherein R1, R2, R3, R4 and W are defined as per formula (A), radicals R1, R2 and R3 on both radicals $M_{R3}6G$-$NR_1R_2$—S being either identical or different, as well as one of their pharmaceutically-acceptable salts.

In a preferred embodiment, Y and Z in the radical R3 are oxygen. In another preferred embodiment, R in the radical R3 is a $C_2$-$C_6$ alkyl, branched or unbranched, saturated or unsaturated, preferably a $C_2$-$C_3$ alkyl, branched or unbranched, saturated or unsaturated, preferably saturated. In a particular embodiment, R3 is Y(C=Z)R with R being a $C_1$-$C_6$ alkyl group, linear or branched, saturated or unsaturated, preferably in $C_1$-$C_3$. In another particular embodiment, R3 is YR with R being a $C_2$-$C_6$ alkyl group, linear or branched, saturated or unsaturated, preferably in $C_2$-$C_3$.

In a preferred embodiment, R4 represents a —$(CH_2)_n$—C(O)—NH— group or —$(CH_2)_n$—NH—C(O), wherein n is an integer comprised between 1 and 8, preferably between 1 and 4.

Preferred compounds according to the invention are compounds of formulae (A) to (D), wherein compounds present one or several following characteristics:

the R3 group represents —OR, where especially R is an ethyl or isopropyl; and/or R2 is a hydrogen; and/or
R1 is a linear alkyl —$(CH_2)_2$— group; and/or
R4 is a —$(CH_2)_2$—C(O)—NH— group; and/or
W represents naltrindole.

Notably, the present invention relates to compounds of formulae (A) to (D) wherein:
R2 is a hydrogen and R1 is a linear alkyl —$(CH_2)_2$— group; and/or
R2 is a hydrogen and R3 represents —OR, where R is especially an ethyl or isopropyl; and/or
R4 is a —$(CH_2)_2$—C(O)—NH— group and W represents naltrindole; and/or
R1 is a linear alkyl —$(CH_2)_2$— group and R3 represents —OR, where R is especially an ethyl or isopropyl; and/or
R1 is a linear alkyl —$(CH_2)_2$— group, R2 is a hydrogen and R3 represents —OR, where R is especially an ethyl or isopropyl.

In a specific embodiment, the compound has the formula (B) and both R2 are hydrogen and both R1 are linear alkyl —$(CH_2)_2$—. In another specific embodiment, the compound has the formula (C) and R2 is a hydrogen, R1 is a linear alkyl —$(CH_2)_2$— group and R4 a —$(CH_2)_2$—C(O)—NH— group.

Asymmetric carbons comprised in formulae (A) to (D) may be of R or S configuration.

Dimeric preferred compounds are represented in structures (I), (II) or (III).

(I): M3iPro-6G-cya-cya-M3iPro-6G (II): M3Et-6G-cya-cya-M3Et-6G (III): M3Et-6G-cya-3MP-NTI.

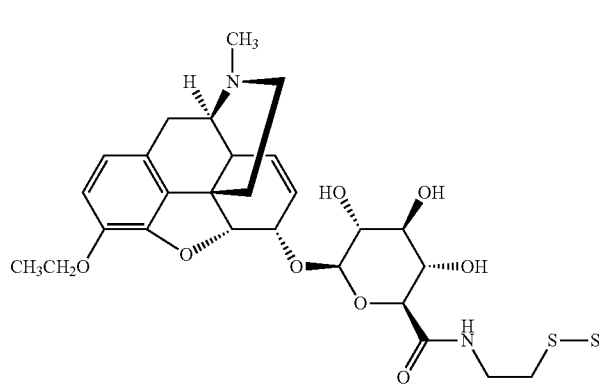
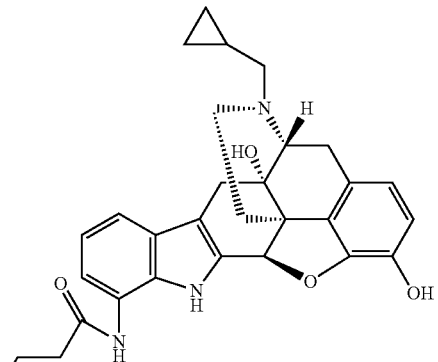

The ethyl group may be replaced by a methyl to give the compound C6G-cya-3 MP-NTI.

Compounds of the present invention may be prepared using methods known from the person having ordinary skill in the art.

The invention relates to a compound according to the invention as a drug.

The invention also relates to a pharmaceutical composition containing as active principle one of the above described compounds or one of its pharmaceutically acceptable salts, such as for instance and not limitatively an acetate, a sulfate or a chlorhydrate.

The pharmaceutical composition according to the invention will appear under an appropriate form, depending on the route of administration:
- the parenteral administration, for instance, through injectable preparation by subcutaneous injection or intravenous injection or intramuscular injection;
- the oral administration, for instance, through pills, capsules, powders, granules, oral solutions or suspensions, either with an immediate release or a prolonged release or even a delayed release;
- the topic administration, and especially the transdermic one, for instance through patch, ointment or gel;
- the intranasal administration, through aerosols and sprays;
- the rectal administration, for instance through suppositories;
- the perlingual administration;
- the intraocular administration.

The pharmaceutically convenient vehicle may be selected among currently used vehicles for each mode of administration.

In an embodiment, the composition may include another active principle.

The invention relates to the use of a compound of formula chosen among formulae (A) to (D) and (I) to (III) or one of its pharmaceutically acceptable salts for the manufacture of a drug dedicated to the treatment of pain, in particular acute pain, chronic pain, neuropathic pain, muscular pain, bone pain, postoperative pain, migraine, cancer-related pain, lumbalgia, arthrosic pain, diabetes-related pain or pain associated to AIDS. The present invention also relates to the use of a compound of formula chosen among formulae (A) to (D) and (I) to (III) or one of its pharmaceutically acceptable salts for the manufacture of a drug dedicated to treatment for sexual dysfunctions and especially premature ejaculation.

The present invention relates to a method of treatment of pain in a subject comprising administering a therapeutically efficient dose of a compound of formula chosen among formulae (A) to (D) and (I) to (III) or one of its pharmaceutically acceptable salts. Particularly, pain is acute pain, chronic pain, neuropathic pain, muscular pain, bone pain, postoperative pain, migraine, cancer-related pain, lumbalgia, arthrosic pain, diabetes-related pain or pain associated to AIDS. Beside, the present invention relates to a method of treatment for sexual dysfunctions and especially premature ejaculation in a subject, comprising administering a therapeutically efficient dose of a compound of formula chosen among formulae (A) to (D) and (I) to (III) or one of its pharmaceutically acceptable salts.

The present invention further relates to a compound of formula chosen among formulae (A) to (D) and (I) to (III) or one of its pharmaceutically acceptable salts for the treatment of pain or the treatment of sexual dysfunctions.

DESCRIPTION OF FIGURES

FIG. 2: Analgesic activity of compounds in the tail flick test.

FIG. 3: Analgesic activity of compounds in the hot plate test.

The invention is not limitatively illustrated through examples below.

EXAMPLES

A. Synthesis

Figure 1:
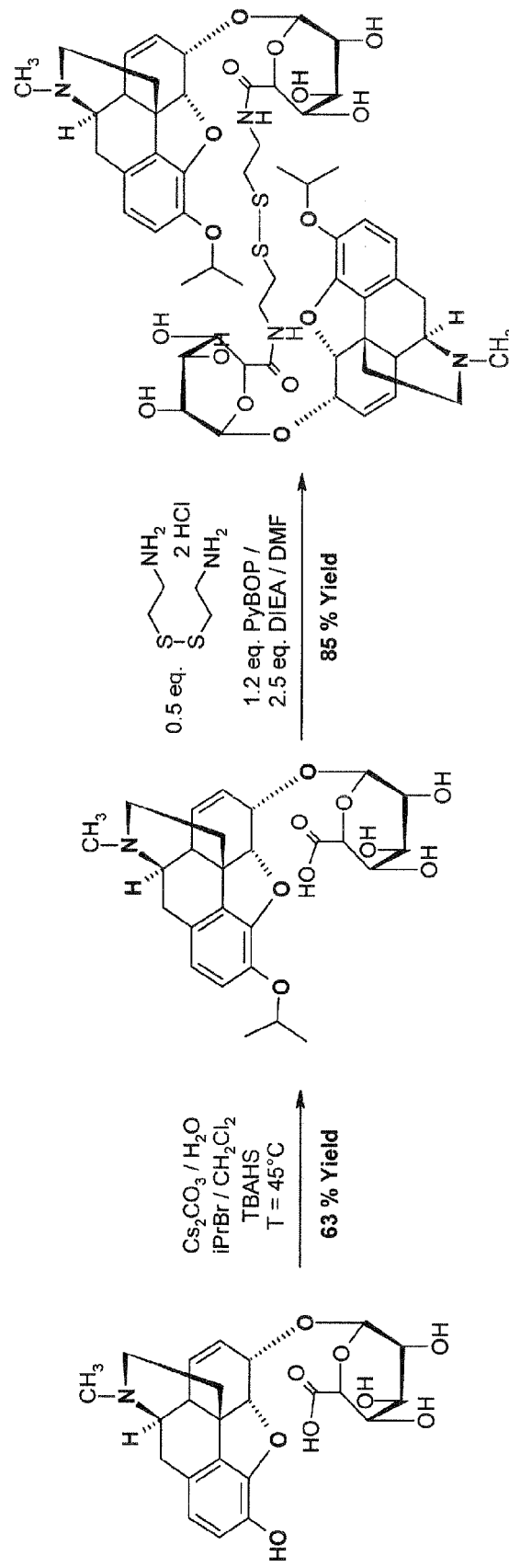
FIG. 1: Synthesis of C6G-Cya, M3Et-6G-Cya, M3Et-6G-Cya-Cya-M3Et-6G, M3iPro-6G-cya-cya-M3iPro-6G and M3Et-6G-cya-3 MP-NTI.
Figure 1:
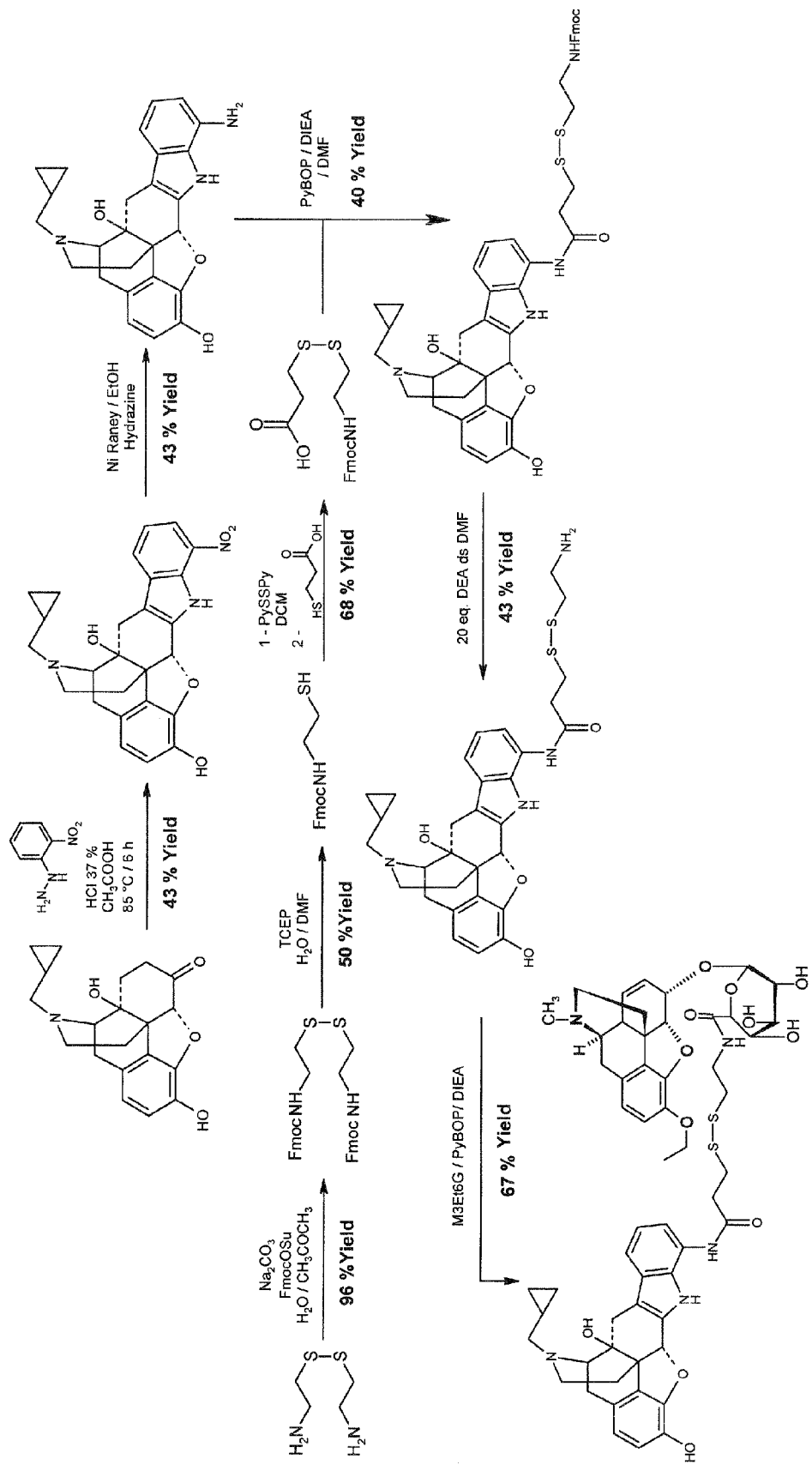

The different processes of synthesis implemented to obtain the Considered Products are detailed hereunder. Reactional pathways are shown on FIG. 1.

Reactions were followed by reversed phase high-performance liquid chromatography (HPLC) and MALDI-TOF mass spectrometry. The products were identified and their purity determined by reversed phase high-performance liquid chromatography (HPLC) and mass spectrometry.

Example 1

C6G-Cya Synthesis

In a reactor, 2 molar equivalents of cysteamine were dissolved into anhydrous dimethylformamide (DMF) at 138 g/l. 1 molar equivalent of commercial codeine-6-glucuronide. TFA was added after dissolution into anhydrous DMF at 47 g/l.

4 molar equivalents of diisopropylethylamine (DIEA) were added and the reactor placed into an ice bath (0° C.). 1.2 molar equivalents of benzotriazole-1-yl-oxy-tris-pyrrolidinophosphonium hexafluorophosphate (PyBOP) previously solubilized into DMF at 225 g/l were dripped into the reaction mixture, then stirred at room temperature during 3 hours.

The disulfide bridge was then reduced by adding 2.5 molar equivalents of tris(2-carboxyethyl)phosphine (TCEP) previously solubilized into water/TFA0.1% at 214 g/l. After 2 hours of reaction, the product was purified by preparative HPLC.

10.3 mg of C6G-cya were obtained after lyophilisation: [M+H]+=535-MTFA=648-Purity: 98%-Yield=93%.

Example 2

Synthesis of M3Et-6G-cya

Synthesis of M3ET-6G

In a reactor, 1 molar equivalent of morphine-6-glucuronide.$2H_2O$ (M6G) was poured and solubilized in water at 100 g/l. 5 equivalents of cesium carbonate were added and the mixture was stirred during 5 minutes at room temperature.

A volume of dichloromethane identical to the volume of water was added to the mixture. 5 equivalents of bromoethane and 2 equivalents of tetrabutylammonium hydrogen sulfate (TBAHS) were successively added. Stirring was maintained at room temperature during 72 hours. The product was purified by preparative HPLC.

A Nuclear Overhauser Effect (NOE) experimentation by proton Nuclear Magnetic Resonance (NMR) showed that the ethyl group was carried by the oxygen atom in position 3 of the morphine derivative. In fact, the controlled irradiation of the ethyl group disturbed the signals of phenol aromatic protons.

45.8 mg of M3Et-6G were obtained: [M+H]+=490-$M_{TFA}$=603-Purity: 93%-Yield=55%.

Synthesis of M3Et-6G-cya

In a reactor, 2 molar equivalents of cysteamine.dihydrochloride were solubilized into DMF at 71 g/l. 1 equivalent of M3Et6G previously solubilized into DMF at 96 g/l was added. The mixture was diluted with DMF and 4 molar equivalents of DIEA were added. The reactor was cooled to 0° C. and 1.2 molar equivalents of PyBOP previously solubilized into DMF at 23 g/l were dripped.

Stirring was maintained at room temperature during 3 hours, then 2.5 molar equivalents of TCEP solubilized into water/TFA 0.1% at 21 g/l were added. After 4 hours of stirring, the reduction ended. The product was purified by preparative HPLC.

46.9 mg of M3Et-6G-cya were obtained: [M+H]+=549-$M_{TFA}$=662-Purity: 95%-Yield=89%.

Example 3

Synthesis of M3Et-6G-cya-cya-M3Et-6G

In a reactor, 1 molar equivalent of cysteamine.dihydrochloride was solubilized into DMF at 86 g/l. 2 molar equivalents of M3Et-6G-cya previously solubilized into DMF at 97 g/l were added. 5 molar equivalents of pure DIEA was then introduced and the mixture was cooled to 0° C. in an ice bath. 2.4 molar equivalents of PyBOP solubilized into DMF at 22.9 g/l were dripped. Stirring was maintained at room temperature during 3 hours. Then the product was purified by preparative HPLC.

40.5 mg of M3Et-6G-cya-cya-M3Et-6G dimer were obtained: [M+H]+=1096-$M_{TFA}$=1322-Purity: 95%-Yield=81%.

Example 4

Synthesis of M3iPro-6G-cya-cya-M3iPro-6G

Synthesis of M3iPro-6G

In a flask of 10 ml, 1 molar equivalent of M6G is solubilized in water at 100 g/l. 5 molar equivalents of cesium carbonate, 2 molar equivalents of TBAHS, 1 ml of dichloromethane and 5 molar equivalents of bromoisopropane are added. The mixture is stirred at 45° C., reflux of dichloromethane, overnight.

Dichloromethane is evaporated and the product is purified by preparative HPLC.

61.7 mg of M3lpro6G are obtained: [M+H]+=504-$M_{TFA}$=617-Purity: 95%-Yield=63%.

Synthesis of M3iPro-6G-cya-cya-M3iPro-6G

In a Falcon tube, 1 molar equivalent of cysteamine.dihydrochloride is solubilized into DMF at 11.2 g/l. 2 molar equivalents of M3iPro-6G previously solubilized into DMF at 100 g/l are added. 5 molar equivalents of pure DIEA are then introduced and the mixture is cooled to 0° C. and stirred during 5 minutes. Then 2.4 molar equivalents of PyBOP previously solubilized into DMF at 240 g/l are added and the mixture is stirred at room temperature during 1 h.

Dimer is purified by preparative HPLC.

46.4 mg of M3iPro-6G-cya-cya-M3iPro-6G are obtained: [M+H]+=1123-$M_{TFA}$=1350-Purity: 95%-Yield=85%.

Example 5

Synthesis of M3Et-6G-cya-3 MP-NTI

Synthesis of 7'-Nitronaltrindole

In a flask, 1 molar equivalent of Naltrexone HCl $2H_2O$ and 1 molar equivalent of (2-nitrophenyl)-hydrazine are introduced in a 50/50 mixture of hydrochloric acid 37% and glacial acetic acid at 57 g/l. The mixture is stirred during 6 h30 at 85° C. and then cooled at 0° C., neutralized with a saturated $NaHCO_3$ solution and extracted 3 times by ethyl acetate. Organic phases are pooled, dried on sodium sulfate, filtered and evaporated under reduced pressure. The obtained solid is then purified by preparative HPLC.

90 mg of 7'-nitronaltrindole are obtained: [M+H]$^+$=460-M$_{TFA}$=573-Purity: 92%-Yield=43%.

Synthesis of 7'-aminonaltrindole

In a Falcon tube of 50 ml, 1 molar equivalent of 7'-nitronaltrindole solubilized into ethanol at 34.6 g/l is introduced. An excess of Raney nickel (50% in water suspension) and 10 molar equivalents of aqueous hydrazine are dripped. After 1 h of reaction, the mixture is centrifuged, the alcohol phase is recovered and ethanol is evaporated under reduced pressure. The obtained residuum is re-solubilized in a minimal amount of water (TFA 0.1%)/acetonitrile (TFA 0.1%) 50/50 and injected in preparative HPLC.

44.1 mg of product are obtained: [M+H]$^+$=430-M$_{TFA}$=657-Purity: 95%-Yield=43%.

Synthesis Fmoc-cysteamine-3 MP

In a flask, 2 molar equivalents of Fmoc-OSu are solubilized into acetone at 320 g/l. 1 molar equivalent of cystamine 2HCl and 1.6 molar equivalents of sodium carbonate are added with a water volume identical to the acetone. The mixture harden. A mixture water/50/50 is added for doubling the solvent volume.

After 2 h30 stirring at room temperature, acetone is evaporated with rotavapor and the obtained suspension is solubilized into dichloromethane. The aqueous phase is extracted by dichloromethane and the organic phases washed successively with KHSO$_3$ and saturated NaCl.

The final organic phase is then dried on sodium sulphate, filtered and evaporated under reduced pressure for providing 2.53 g of Fmoc-cystamine: [M+H]$^+$=598-Purity: 95%-Yield=96%.

The disulfide bridge reduction is carried out by solubilizing 1 molar equivalent of Fmoc-cystamine into DMF at 25 g/l and adding 2.5 molar equivalents of Tris(2-carboxyethyl)phosphine (TCEP) previously solubilized into water (0.1% TFA) at 400 g/l. After 1 h stirring at room temperature, a large excess of water is added and the mixture is extracted with dichloromethane. The organic phases are pooled, washed with saturated NaCl, dried on Na$_2$SO$_4$ and filtered on fritted. Dichloromethane is evaporated. The product is then precipitated by adding water (0.1% TFA), filtered on fritted and solubilized into a mixture of H$_2$O (0.1% TFA)/ACN (0.1% TFA) (25/75) then lyophilized.

252 mg of product are obtained [M+H]$^+$=300-Purity: 95%-Yield=50%.

3 molar equivalents of 2-2'-dithiodipyridine solubilized into dichloromethane at 122 g/l are cooled at 0° C.

1 molar equivalent of Fmoc-cysteamine previously solubilized into dichloromethane at 18 g/l is dripped during 10 minutes.

After 3 h of reaction at room temperature, the mixture is cooled at 0° C. and 5.5 molar equivalents of d3-mercaptopropionic acid diluted into dichloromethane at 18 μl/ml are dripped during 20 minutes. After an overnight reaction at room temperature, dichloromethane is evaporated under reduced pressure. The obtained residuum is purified by preparative HPLC.

231 mg of Fmoc-cysteamine-3 MP are obtained: [M+H]$^+$=400-Purity: 95%-Yield=68%.

Synthesis of cysteamine-3 MP-7' aminonaltrindole 1 molar equivalent of 7' aminonaltrindole is solubilized into DMF at 70 g/l. 2.1 molar equivalents of Fmoc-cysteamine-3 MP solubilized into DMF at 66 g/l and 6 molar equivalents of pure DIEA are added. The mixture is cooled at 0° C. without stirring. 1.1 molar equivalents of PyBOP previously solubilized into DMF at 200 g/l are dripped. After 60 minutes of reaction, the mixture is purified by preparative HPLC. 22.5 mg of Fmoc-cysteamine-3 MP-7' aminonaltrindole are obtained: [M+H]$^+$=815-M$_{TFA}$=928-Purity: 94%-Yield=36%.

1 molar equivalent of Fmoc-cysteamine-3 MP-7' aminonaltrindole is solubilized into DMF at 15 g/l. 20 molar equivalents of pure DEA are added and the mixture is stirred during 30 minutes at room temperature.

The mixture is purified by preparative HPLC.

9.3 mg of cysteamine-3 MP-7' aminonaltrindole are obtained: [M+H]$^+$=593-M$_{TFA}$=820-Purity: 81%-Yield=43%.

Synthesis of M3Et-6G-cya-3 MP-NTI 1 molar equivalent of Cya-3 MP-7' aminonaltrindole is solubilized into DMF at 70 g/l. 1 molar equivalent of M3Et-6G solubilized into DMF at 70 g/l is added with 5 molar equivalents of DIEA. The mixture is cooled at 0° C. and 1.2 molar equivalents of PyBOP solubilized into DMF at 200 g/l are dripped in the mixture. After 45 minutes of stirring at room temperature, the mixture is purified by preparative HPLC.

11 mg of chimera are obtained: [M+H]$^+$=1064-M$_{TFA}$=1291-Purity: 95%-Yield=67%.

B. Affinity Study of Opioid Receptor

B.1/Experimental Procedure

The affinity of M6G to C6G-cya, M3Et-6G-cya and M3Et-6G-cya-cya-M3Et-6G derivatives has been compared for each of the three sub-types of μ, δ and κ opioid receptors.

In order to determine the affinity to μ receptors, homogenates of cell membrane (human μ receptors transfected on HEK-293 cells) were incubated at 22° C. during 120 nm with 0.5 nM of [3H][D-Ala, N-MePhe, Gly(ol)]enkephalin (DAMGO) either with or without one of the compound(s) according to the invention into a buffer containing 50 mM Tris-HCl (pH 7.4) and 5 mM MgCl2.

In order to determine the affinity to K receptors, homogenates of guinea-pigs cerebellum (250 μg of protein) were incubated at 22° C. during 80 nm with 0.7 nM of [3H]U-69593 either with or without one of the compound(s) according to the invention into a buffer containing 50 mM Tris-HCl (pH 7.4), 10 mM MgCl2 and 1 mM of EDTA.

In order to determine the affinity to δ receptors, homogenates of cell membrane (human Mu receptors transfected on CHO cells) were incubated at 22° C. during 120 nm with 0.5 nM of [3H]DADLE either with or without one of the compound(s) according to the invention into a buffer containing 50 mM Tris-HCl (pH 7.4) and 5 mM MgCl2.

The non specific binding was determined in the presence of 10 μM of naltrexone. After incubation, samples were rapidly filtered through glass fibers (GF/B, Packard), previously incubated with 0.3% of polyethyleneimine and rinsed several times with 50 mM of cold Tris-HCl using a "96-sample cell harvester" (Unifilter, Packard). Filters were afterwards dried and the radioactivity was counted.

The agonist/antagonist activity on K receptors of compounds according to the invention was estimated by using prostatic segments of rabbits' deferens vas, stretched and stimulated by an electric current of 0.1 Hz during 1 msec.

In order to test an agonist activity, a response control (peak of contractions of the tissue) was obtained by exposing tissues to a high concentration (0.1 μM) in U-69593, which is a specific K receptor agonist.

Tissues were then exposed to growing concentrations of the compound according to the invention or to the specific agonist. The various concentrations were cumulated and each concentration was maintained in contact with the tissue until a stable response was obtained or during a maximum of 15 nm.

If a characteristic response of the agonist was noted (i.e. an inhibition of the contractions), an antagonist of reference, the nor-binaltorphimine (nor-BNI, 0.001 µM), was tested at the highest concentration of the compound according to the invention to confirm the role of κ receptors in the response.

In order to test an antagonist activity, a response control (peak of contraction of the tissue) was obtained by exposing tissues to a high concentration (0.1 µM) in specific agonist U-69593.

Tissues were then exposed to growing concentrations of the compound according to the invention or to the specific agonist. The various concentrations were cumulated and each concentration was maintained in contact with the tissue until a stable response was obtained or up to 15 nm.

An antagonist response was observed when the amplitude of peaks of contractions provoked by electric stimulation was similar to the one observed with the nor-BNI.

The measured parameter was a maximal change of amplitude of the peaks of contractions provoked by electric stimulation with various concentrations of the compound.

B.2/Results

The results of affinity to µ, δ and κ receptors are detailed in the Table 1 below:

TABLE 1

| Compound | Ki (nM) µ Receptor | Ki (nM) δ Receptor | Ki (nM) κ Receptor |
|---|---|---|---|
| Morphine | 12 | 150 | 150 |
| C6G-cya | 11 | NC | 100 |
| M3Et-6G-cya | 13 | NC | 220 |
| M3Et-6G-cya-cya-M3Et-6G | 14 | >1000 | 25 |

NC: Not considered because lower than 25% of inhibition to highest concentrations.

The results show:

An affinity to µ receptors for compounds according to the invention that is similar to morphine.

A loss of affinity for compounds according to the invention to δ receptors when compared with morphine.

An affinity of C6G-cya and M3Et-6G-cya monomer compounds for κ receptors similar to the one of morphine and an improvement of affinity (factor 6) of M3Et-6G-cya-cya-M3Et-6G dimer.

The agonist/antagonist activity of the compound M3Et-6G-cya-cya-M3Et-6G was measured as above described (§ B1): the compound according to the invention behaves as a κ receptor antagonist.

Results of agonist/antagonist activity are shown below in Table 2:

TABLE 2

Agonist/antagonist activity on κ receptor:

Evaluation of agonist activity:

| Compounds | Response Control at U-69593 (0.1 µM) | Response to an increasing concentration of the compound | | | | +nor-BNI (1 nM) |
|---|---|---|---|---|---|---|
| M3Et-6G-cya-cya-M3Et-6G | 100 | 0.03 µM 0 | 0.3 µM 0 | 3 µM −4 | 30 µM −3 | 10 µM NC |
| U-69593 | 100 | 0.01 µM 18 | 0.03 µM 46 | 0.1 µM 100 | | 0.1 µM −6 |

Evaluation of antagonist activity:

| Compounds | Response Control at U-69593 (0.1 µM) | Response to an increasing concentration of the compound | | | |
|---|---|---|---|---|---|
| M3Et-6G-cya-cya-M3Et-6G | 100 | 0.03 µM 100 | 0.3 µM 100 | 3 µM 92 | 30 µM 71 |
| nor-BNI | 100 | 0.1 nM 80 | 0.3 nM 55 | 1 nM −1 | |

Responses are indicated in % of the response control at U-69593 (decrease of the amplitude of contractions).

C. Study of Analgesic Activity

C.1 Operative Mode

The analgesic activity was determined through both the "Tail flick" and the "Hot plate" tests.

The "Tail flick" test (test of D'Amour & Smith, 1941, Pharmacol Exp Ther; 72: 74-79) consists in placing the tail of a mouse, after administration of a product, in front of an infrared source in order to produce a nociceptive stimulus (a surface temperature of 55° C.). The reaction time (RT) of the mouse (latency between the start of the light beam and the moment the mouse withdraws its tail) was measured in duplicate at 8 times spread from 15 nm to 480 nm after administration of the product. A maximal 10 second-period has been chosen as the maximal reaction time in order to avoid any tissue damage for the animal.

Products were intravenously-administered at doses comprised between 0.5 and 8 mg/kg (8 mice per group).

Two measures of reaction time were realized before administration of the product for each mouse so as to establish a base line.

The "Hot plate" test consists in placing a mouse on a hot plate at 54° C. and in measuring the apparition of one of the following behaviours:

jump involving at least one of the four paws
licking of front or rear paws,
exceeding a 30 second period on the hot plate
activation of the speed of displacement.

The withdrawal time was measured in duplicate at different times spread from 15 nm to 360 nm after injection of the product.

A base line was determined for each mouse before administration of the tested product.

Products were intravenously administered at doses comprised between 0.5 and 8 mg/kg (8 mice per group).

C.2/Results

With respect to the tail flick test, obtained results for morphine, M3Et-6G-cya, M3Et-6G-cya-cya-M3Et-6G, C6G-cya-cya-C6G, M3iPro-6G-cya-cya-M3iPro-6G and M3Et-6G-cya-3 MP-NTI cya-M3Et-6G, are indicated as the average per group of % MPE±S.E.M and shown in FIG. 2.

The MPE % represents the percentage of possible maximal effect and corresponds to the following formula:

$$\% \, MPE = \frac{(TR_{post\text{-}administration} - TR_{pre\text{-}administration})}{(TR_{max} - TR_{pre\text{-}administration})} \times 100$$

For each product, the ED50 (active dose for 50% of animals) and the AUC (area under curve) were calculated and represented below in tables 3 (ED50) and 4 (AUC).

TABLE 3

ED50 calculated on the basis of the tail flick test:
ED50 mg/Kg

| Compound | Max Effect | ED50 |
|---|---|---|
| Morphine | 30 min | 3.273 |
| M(3Et)6G-Cya | 120 min | 2.042 |
| M3Et-6G-cya-cya-M3Et-6G | 120 min | 1.318 |
| C6G-cya-cya-C6G | 30 min | ND |
| M3iPro-6G-cya-cya-M3iPro-6G | 60 min | 1.7 |
| M3Et-6G-cya-3MP-NTI | 120 min | 2.9 |

ND: undetermined (lack of analgesic response)

TABLE 4

AUC calculated on the basis of the tail flick test:
AUC

| Dose (mg/Kg) | — | — | 1.7 | 3.4 | 6.8 |
|---|---|---|---|---|---|
| Morphine | — | — | 60.62 | 589.54 | 1529.18 |
| Dose (mg/kg) | 0.5 | 1 | 2 | 4 | 8 |
| M(3Et)6G-Cya | — | 1047.85 | 2538.93 | 5012.90 | 6059.22 |
| M3Et-6G-cya-cya-M3Et-6G | 617.79 | 1233.75 | 4824.51 | 5915.16 | 5817.46 |
| C6G-cya-cya-C6G | 440 | 147 | 500 | 281 | 251 |
| M3iPro-6G-cya-cya-M3iPro-6G | — | 1223 | 4242 | 5685 | — |
| M3Et-6G-cya-3MP-NTI | — | — | 2576 | 4410 | 5733 |

With respect to the hot plate test, obtained results for morphine, M3Et-6G-cya and M3Et-6G-cya-cya-M3Et-6G, are indicated as the average per group of % MPE±S.E.M and shown in FIG. 3.

For each product, the ED50 (active dose in 50% of animals) and the AUC (area under the curve) were calculated and represented below in tables 5 (ED50) and 6 (AUC).

TABLE 5

ED50 calculated on the basis of the hot plate test:
ED50 mg/Kg

| Compound | Effet max | ED50 |
|---|---|---|
| Morphine | 30 min | 3.802 |
| M(3Et)6G-Cya | 120 min | 2.754 |
| M3Et-6G-cya-cya-M3Et-6G | 120 min | 1.349 |

TABLE 6

AUC calculated on the basis of the hot plate test:
AUC

| Dose (mg/Kg) | — | — | 1.7 | 3.4 | 6.8 |
|---|---|---|---|---|---|
| Morphine | — | — | 931.55 | 986.99 | 4613.09 |
| M(3Et)6G-Cya | — | 1912.70 | 4962.00 | 9618.55 | 16359.84 |
| M3Et-6G-cya-cya-M3Et-6G | 1182.74 | 1437.18 | 4928.30 | — | — |

Results show that compounds according to the invention have an analgesic activity at least superior than the one showed by morphine. Actually, their ED50 is comprised between 1.3 and 2 mg/kg, compared with 3.3 mg/kg for morphine.

Moreover, the duration of the analgesic activity is much longer for compounds M3Et-6G-cya and M3Et-6G-cya-cya-M3Et-6G than for morphine. Actually, compounds according to the invention remain at least twice longer active than morphine.

D. Study of Intestinal Transit in Mice

D.1/Operative Mode

Awake mice are force-fed by introducing in the oesophagus of a feeding tube with a 1 ml syringe. 600 µl of gavage paste (notably constituted of activated carbon) are slowly introduced. 30 min after force-feeding, animals are sacrificed. After incision of abdominal wall, the intestines are exposed over all their length. The distance between cardia and rectum is measured (total length) as well as the distance between cardia and marker front.

The effect of compound M3Et-6G-cya-cya-M3Et-6G on constipation was measured at the maximum effect after iv injection at ED50 and then compared to the effect of morphine in the same conditions.

In order to get closer to a clinical case of post-operative pain in which the patient needs an analgesic effect during several hours, the following protocol was used:

Compound M3Et-6G-cya-cya-M3Et-6G and morphine are injected at two-fold ED50.

In order to maintain the maximum analgesia during 6 h30, a morphine dose is injected every hour, possibly corresponding to morphine pump in hospital. It is not necessary to inject supplementary dose of M3Et-6G-cya-cya-M3Et-6G since the activity is maximum during at least 6 hours.

Transit is then measured from 30 min after force-feeding of mice to 6 hours after administration.

A send measure is performed 2 h30 after the last morphine injection or 8 h30 after injection of M3Et-6G-cya-cya-M3Et-6G. Finally, measures are performed 10 h and 12 h after injection of M3Et-6G-cya-cya-M3Et-6G in order to evaluate the return speed to normal transit.

D.2/Results

The transit percentage is calculated as following:

distance of marker×100/total length.

Figure 4:
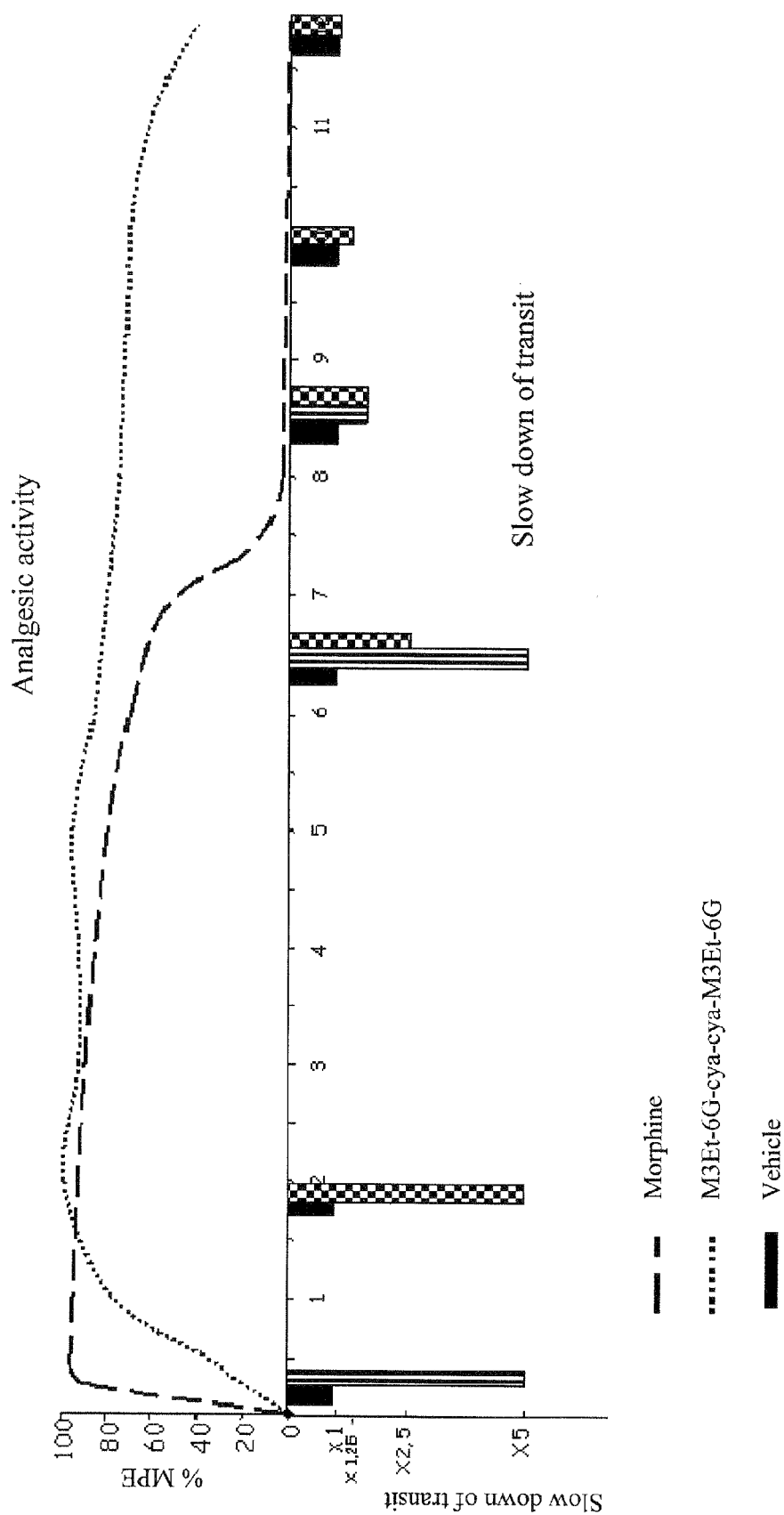
FIG. 4: Effect of compounds on intestinal transit.

Data are shown in FIG. 4.

No significant difference on the transit is observed between compound M3Et-6G-cya-cya-M3Et-6G and morphine at the maximal analgesic effect after injection at ED50 (transit inhibition of about 90%).

In case of maintenance of maximal analgesia during 6 h30, transit inhibition is lower with compound M3Et-6G-cya-cya-M3Et-6G (52 to 56%) in comparison with morphine (82%).

When the analgesic activity is maintained at maximum with morphine, transit is completely stopped. Transit restarts when the morphine injections are stopped, together with a drop of analgesic activity.

In case of compound M3Et-6G-cya-cya-M3Et-6G, transit only slows down whereas the analgesic activity stays maximum. The transit speed becomes normal between 10 and 12 hours with an analgesia of 50%.

The invention claimed is:

1. A compound of formula (A):

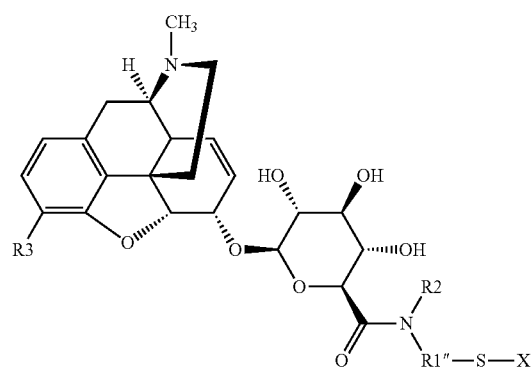

(A)

wherein,
the whole entity (A), except for substituent X, is designated as MR36G-NR1R2-S;
R1 is a saturated $C_1$-$C_{10}$ alkyl group;
R2 is a hydrogen;
R3 is ethoxy or isopropyloxy;
X is hydrogen, a radical —S—$(CH_2)_2$—C(O)—NH-naltrindole, wherein naltrindole is attached to the nitrogen atom at the 7' position of the naltrindole structure, or a radical MR36G-NR1R2-S;

and pharmaceutically acceptable salts thereof, wherein the compound of formula (A) has a longer period of analgesic activity than morphine.

2. The compound according to claim 1, wherein X is a radical —S—$(CH_2)_2$—C(O)—NH-naltrindole, wherein naltrindole is attached to the nitrogen atom at the 7' position of the naltrindole structure, or a radical MR36G-NR1R2-S, wherein radical R1 is identical or different on both radicals MR36G-NR1R2-S.

3. The compound according to claim 2, wherein the compound is selected from the group consisting of formulae (I), (II) and (III) wherein:

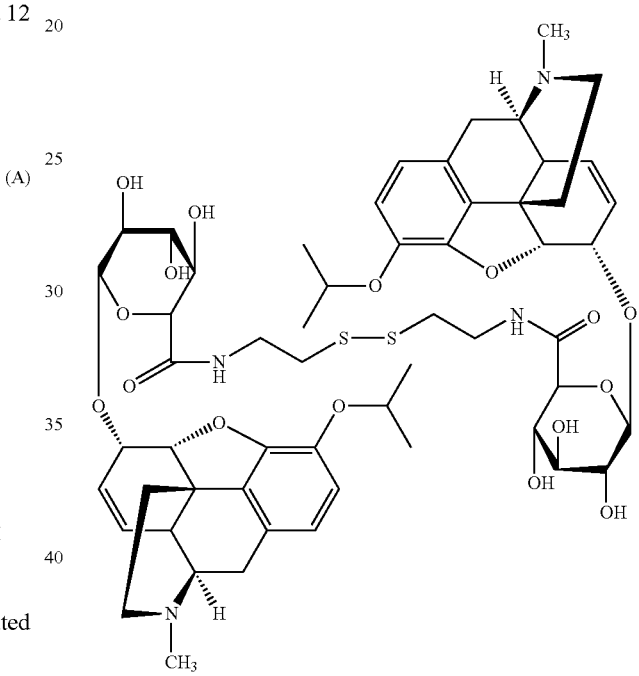

formula (I) is: M3iPro-6G-cya-cya-M3iPro-6G

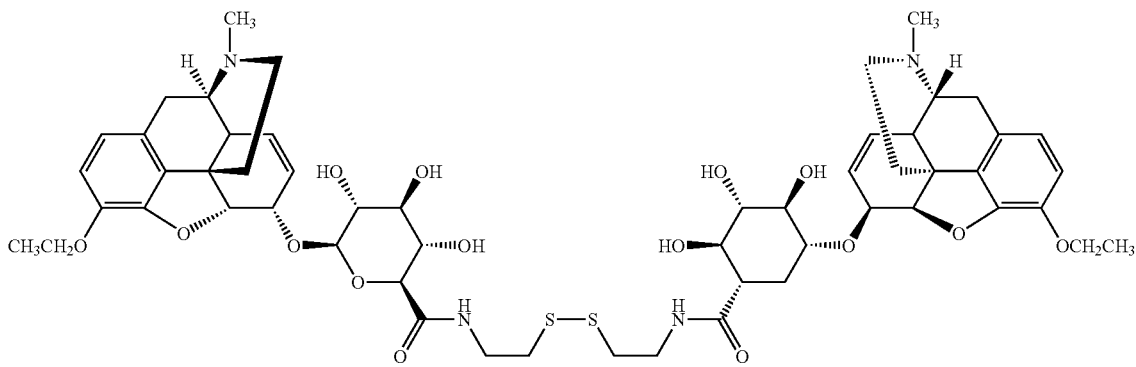

formula (II) is: M3Et-6G-cya-cya-M3Et-6G, and

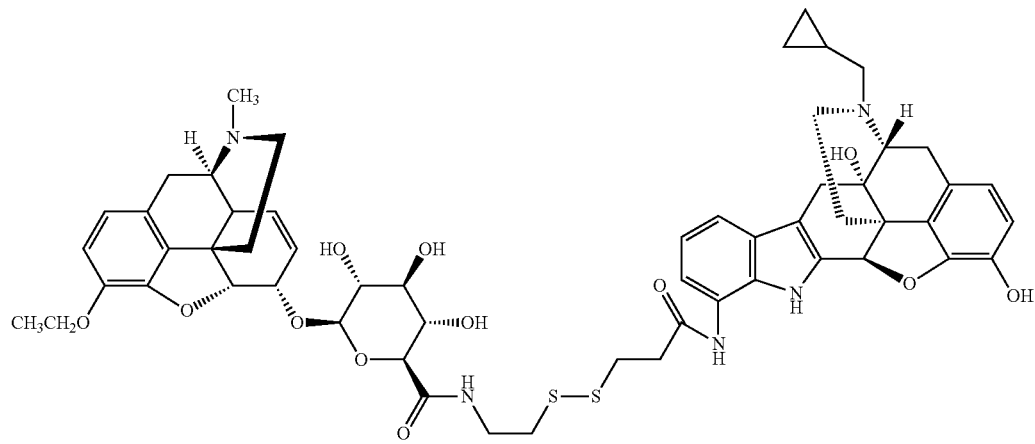

formula (III) is: M3Et-6G-cya-3 MP-NTI.

4. A pharmaceutical composition comprising the compound according to claim 1.

5. A method for treating pain in a subject comprising administering to a subject a therapeutically efficient amount of a compound according to claim 1.

6. The compound according to claim 3, wherein said compound is M3iPro-6G-cya-cya-M3iPro-6G.

7. The compound according to claim 3, wherein said compound is M3Et-6G-cya-cya-M3 Et-6G.

8. The compound according to claim 3, wherein said compound is M3Et-6G-cya-3 MP-NTI.

9. The compound according to claim 1, wherein R1 is a saturated $C_2$ alkyl group and X is hydrogen.

10. The compound according to claim 2, wherein X is —S—$(CH_2)_2$—C(O)—NH-naltrindole, wherein naltrindole is attached to the nitrogen atom at the 7' position of the naltrindole structure.

11. The compound according to claim 2, wherein X is MR36G-NR1R2-S, wherein radical R1 is identical or different on both radicals MR36G-NR1R2-S.

* * * * *

UNITED STATES PATENT AND TRADEMARK OFFICE
CERTIFICATE OF CORRECTION

Page 1 of 4

PATENT NO. : 8,158,764 B2
APPLICATION NO. : 12/444430
DATED : April 17, 2012
INVENTOR(S) : Karine Larbouret, Roger Lahana and Cedric Castex It is certified that error appears in the above-identified patent and that said Letters Patent is hereby corrected as shown below:

Column 4,
Line 48, "δ receptor" should read --δ receptor--.

Columns 5-6,
Formula (B),

"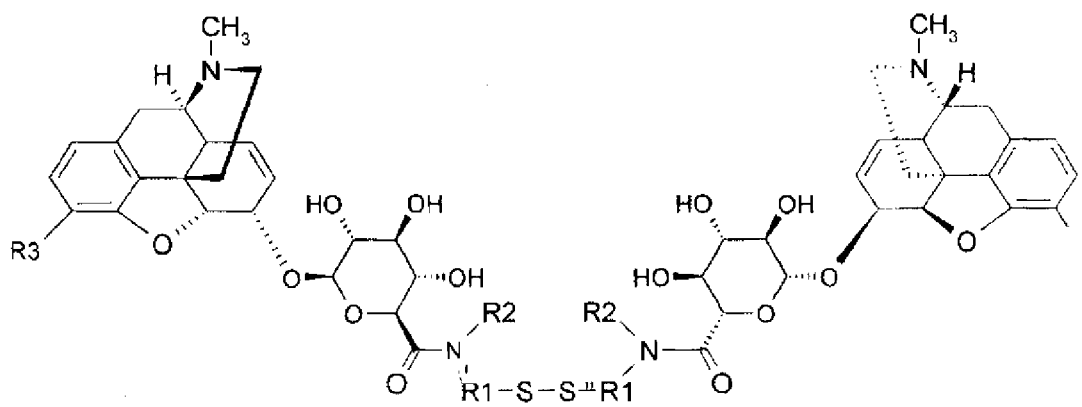"

should read

Signed and Sealed this
Thirty-first Day of July, 2012

David J. Kappos
*Director of the United States Patent and Trademark Office*

CERTIFICATE OF CORRECTION (continued)
U.S. Pat. No. 8,158,764 B2

Columns 5-6,
Formula (B),

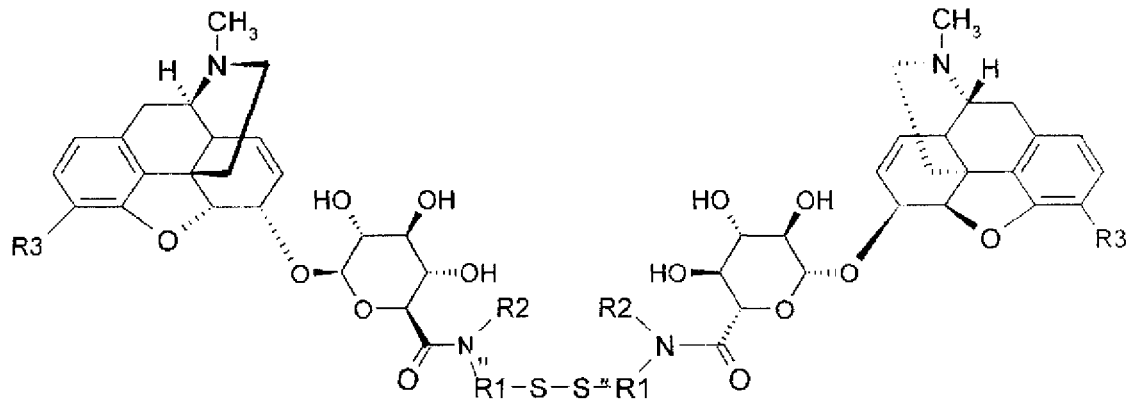

--                                                                                                           --.

Column 7,
Structure (I),

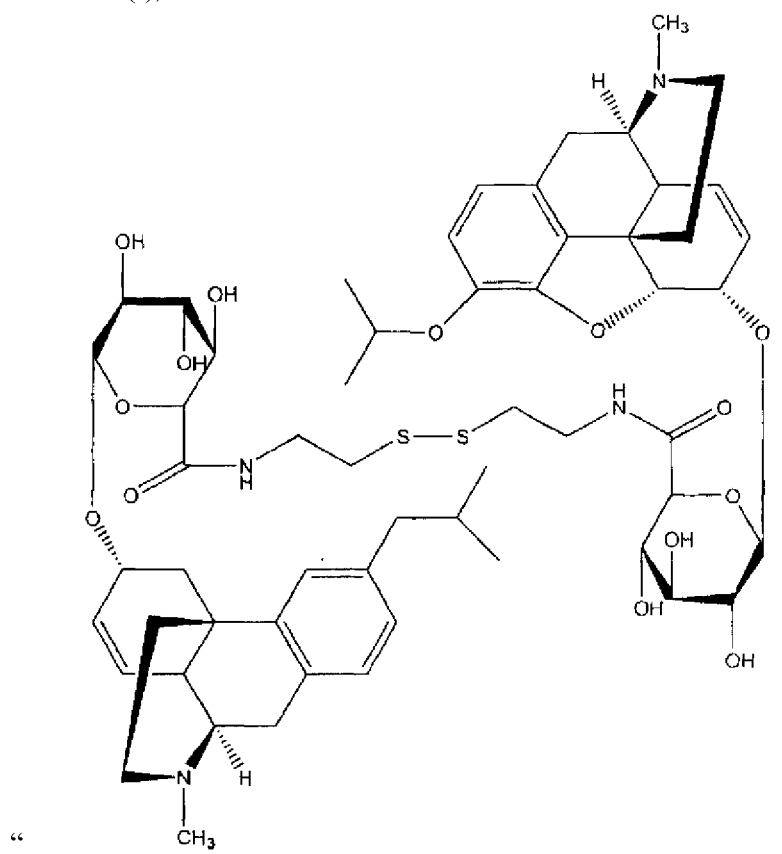

"                                                                    "

should read

CERTIFICATE OF CORRECTION (continued)
U.S. Pat. No. 8,158,764 B2

Column 7,
Structure (I),

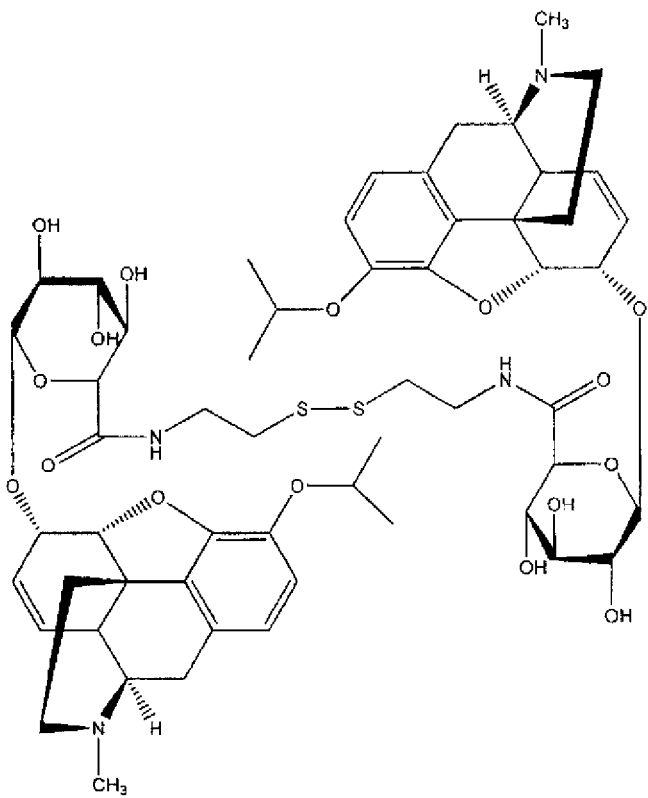

--                                                                    --.

Columns 7-8,
Structure (II),

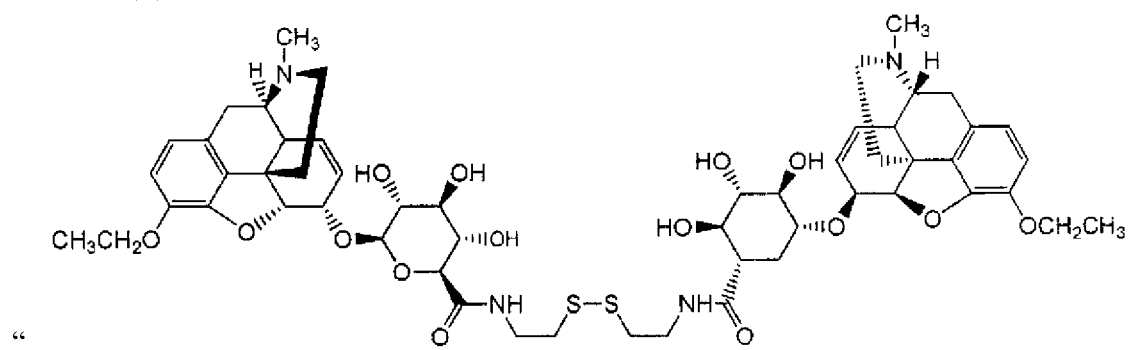

"                                                                     "

should read

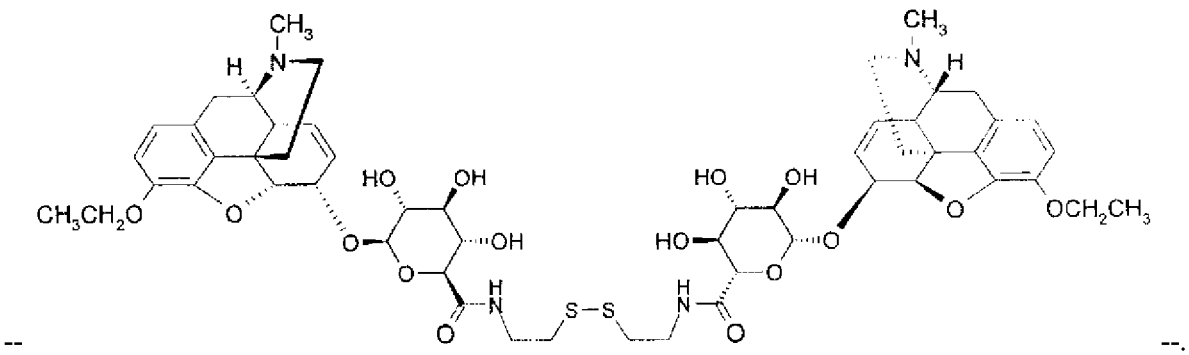

Column 12,
Line 36, "M31pro6G" should read --M3ipro6G--.

Column 14,
Line 41, "K receptors" should read --κ receptors--.
Line 43, "80 nm" should read --80 mn--.
Line 49, "120 nm" should read --120 mn--.
Line 60, "K receptors" should read --κ receptors--.
Line 67, "K receptor" should read --κ receptor--.

Column 15,
Lines 5-6, "15 nm" should read --15 mn--.
Line 11, "K receptors" should read --κ receptors--.
Line 42, "15 nm" should read --15 mn--.

Column 16,
Line 8, "K receptors" should read --κ receptors--.
Line 56, "15 nm to 480 nm" should read --15 mn to 480 mn--.

Column 17,
Line 6, "15 nm to 360 nm" should read --15 mn to 360 mn--.